United States Patent
Kim et al.

(10) Patent No.: US 10,987,245 B2
(45) Date of Patent: Apr. 27, 2021

(54) TEMPERATURE PROVIDING DEVICE

(71) Applicant: NUNAPS INC., Seoul (KR)

(72) Inventors: Dong Ho Kim, Seoul (KR); Dong Wha Kang, Seoul (KR)

(73) Assignee: NUNAPS INC., Seoul (KR)

( * ) Notice: Subject to any disclaimer, the term of this patent is extended or adjusted under 35 U.S.C. 154(b) by 0 days.

(21) Appl. No.: 16/742,188

(22) Filed: Jan. 14, 2020

(65) Prior Publication Data

US 2020/0146882 A1 May 14, 2020

Related U.S. Application Data

(63) Continuation of application No. PCT/KR2018/007948, filed on Jul. 13, 2018.

(30) Foreign Application Priority Data

Jul. 14, 2017 (KR) .................. 10-2017-0089826

(51) Int. Cl.
| | | |
|---|---|---|
| A61F 7/08 | (2006.01) |
| A61F 7/00 | (2006.01) |
| G01K 1/02 | (2021.01) |
| G01K 13/00 | (2021.01) |

(52) U.S. Cl.
CPC .............. *A61F 7/08* (2013.01); *A61F 7/007* (2013.01); *G01K 1/026* (2013.01); *G01K 13/00* (2013.01); *A61F 2007/0052* (2013.01); *A61F 2007/0054* (2013.01); *A61F 2007/0071* (2013.01); *A61F 2007/0086* (2013.01); *A61F 2007/0093* (2013.01); *A61F 2007/0095* (2013.01); *A61F 2007/0096* (2013.01)

(58) Field of Classification Search
CPC combination set(s) only.
See application file for complete search history.

(56) References Cited

U.S. PATENT DOCUMENTS

| | | | |
|---|---|---|---|
| 2005/0288748 A1* | 12/2005 | Li et al. | |
| 2014/0155778 A1* | 6/2014 | Golosarsky | A61B 5/0051 600/557 |
| 2015/0032192 A1* | 1/2015 | Pezzi | A61F 7/007 607/104 |

FOREIGN PATENT DOCUMENTS

| | | |
|---|---|---|
| KR | 10-1991-0019589 A | 12/1991 |
| KR | 10-2010-0098913 A | 9/2010 |
| KR | 10-2013-0036026 A | 4/2013 |
| KR | 10-2014-0042786 A | 4/2014 |

OTHER PUBLICATIONS

International Search Report issued in PCT/KR2018/007948; dated Oct. 18, 2018.

* cited by examiner

*Primary Examiner* — Joseph A Stoklosa
*Assistant Examiner* — Adam J Avigan
(74) *Attorney, Agent, or Firm* — Studebaker & Brackett PC

(57) ABSTRACT

Disclosed is a temperature providing device including a housing body, a plurality of temperature transmitters transmitting different temperatures to an outside of the housing body, and a temperature adjusting unit adjusting a temperature of each of the plurality of temperature transmitters.

15 Claims, 8 Drawing Sheets

TEMPERATURE PROVIDING DEVICE

CROSS-REFERENCE TO RELATED APPLICATIONS

The present application is a continuation of International Patent Application No. PCT/KR2018/007948, filed on Jul. 13, 2018 which is based upon and claims the benefit of priority to Korean Patent Application No. 10-2017-0089826 filed on Jul. 14, 2017. The disclosures of the above-listed applications are hereby incorporated by reference herein in their entirety.

BACKGROUND

Embodiments of the inventive concept described herein relate to a device providing different temperatures to the outside.

For the purpose of treating patients with chronic pain or of examining the senses of a patient, a method of alternately providing the surface of a skin at different temperatures is utilized.

The method of providing a specific temperature to the outside has been used by changing the temperature of water using a device providing a specific temperature to the surface of the patient's skin.

This technical feature is disclosed in Korean Patent Publication No. 10-2010-0098913 (published on Sep. 10, 2010).

However, when a device that provides a specific temperature to the outside by changing the temperature of water is used by a specific number of times or more, it is difficult to set the precise temperature and there may be a delay in changing the temperature.

There is a nerve fiber, which reacts only when the temperature changes rapidly and sharply, in the body; for the purpose of stimulating this, it is necessary to develop a device capable of rapidly changing temperature at specific intervals.

SUMMARY

Embodiments of the inventive concept provide a device capable of providing different temperatures to the outside.

The technical problems to be solved by the present inventive concept are not limited to the aforementioned problems, and any other technical problems not mentioned herein will be clearly understood from the following description by those skilled in the art to which the inventive concept pertains.

According to an exemplary embodiment, a temperature providing device includes a housing body, a plurality of temperature transmitters transmitting different temperatures to an outside of the housing body, a temperature adjusting unit adjusting a temperature of each of the plurality of temperature transmitters, a controller determining a specific temperature to be transmitted to the outside of the housing body and exposing a temperature transmitter having the determined specific temperature among the plurality of temperature transmitters to the outside of the housing body.

Furthermore, the temperature providing device further includes a driving unit moving each of the plurality of temperature transmitters. The controller may expose the temperature transmitter having the determined specific temperature among the plurality of temperature transmitters to the outside of the housing body, using the driving unit.

Moreover, the temperature providing device may be mounted on a body. The controller may expose at least part of the plurality of temperature transmitters to the outside of the housing body by using the driving unit to contact the at least part of the plurality of temperature transmitters to the body and to space a rest of the plurality of temperature transmitters, which are not exposed, from the body.

Also, the plurality of temperature transmitters may include a first temperature transmitter and a second temperature transmitter. The temperature adjusting unit may set the first temperature transmitter to a first temperature and may set the second temperature transmitter to a second temperature different from the first temperature. The controller alternately may expose the first temperature transmitter and the second temperature transmitter to the outside of the housing body, using the driving unit.

Furthermore, the temperature providing device may be mounted on a body. The controller may alternately contact or space the first temperature transmitter and the second temperature transmitter to or from the body, using the driving unit.

Moreover, the temperature transmitter may include at least one heating plate. The temperature adjusting unit may adjust a temperature of the heating plate, using electricity.

Also, the driving unit may include at least one motor. The controller may expose a heating plate having the specific temperature to the outside of the housing body by rotating the at least one heating plate using the motor.

Furthermore, the temperature transmitter may include at least one pipe. The temperature adjusting unit may adjust a temperature of the pipe, using water.

Moreover, the temperature adjusting unit may include a heating part for increasing a temperature of the temperature transmitter and a cooling part for decreasing the temperature of the temperature transmitter.

Also, the cooling part may include at least one cooling fan.

Furthermore, the temperature providing device may further include a temperature measurement unit measuring the temperature of each of the plurality of temperature transmitters.

According to an exemplary embodiment, provided is a method for training pain improvement, which is performed using a temperature providing device according to the disclosed embodiments.

Other details according to an embodiment of the inventive concept are included in the detailed description and drawings.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
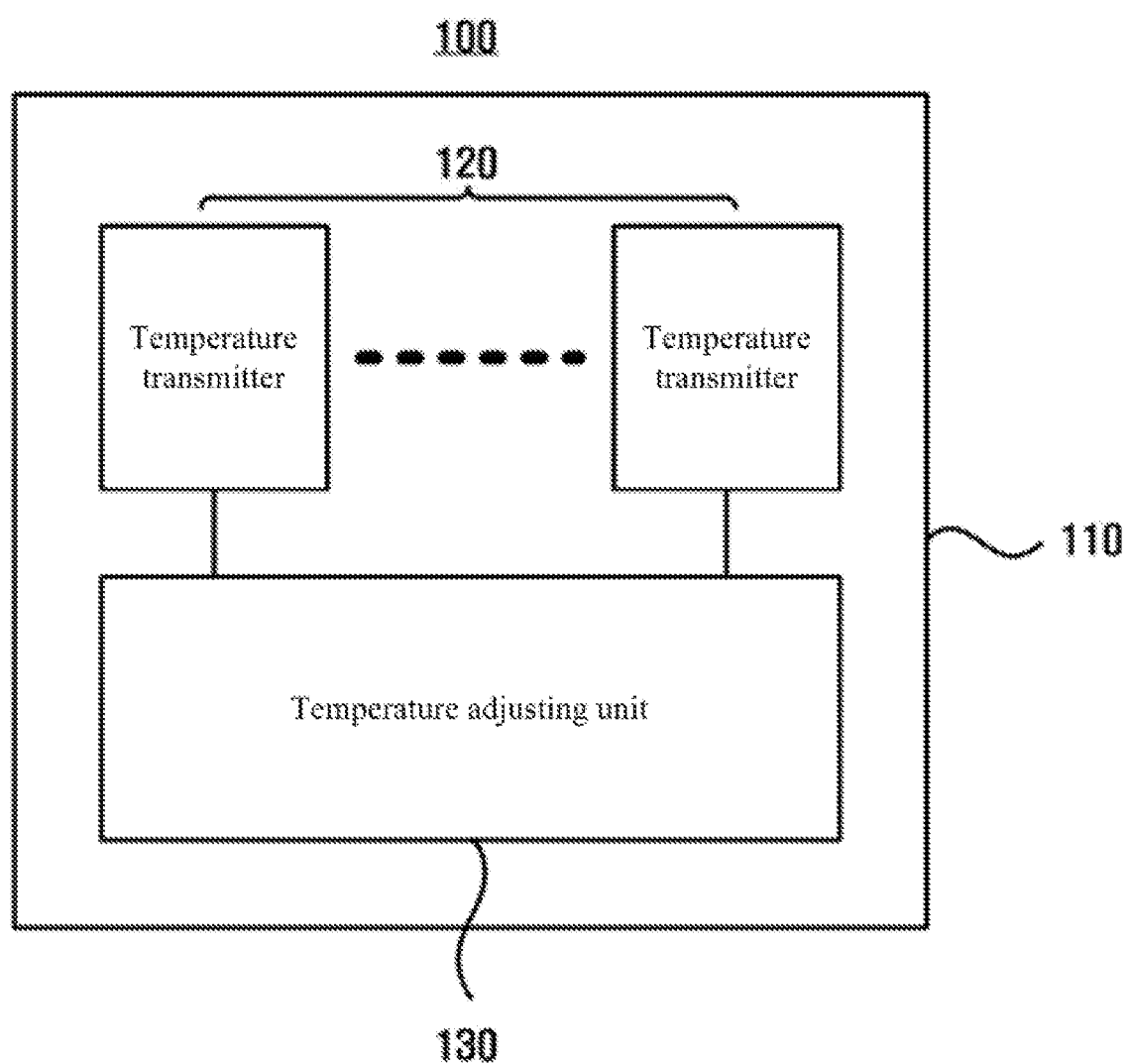
FIG. 1 is a block diagram schematically illustrating a temperature providing device, according to an embodiment.

Advantage points and features of the inventive concept and a method of accomplishing thereof will become apparent from the following description with reference to the following figures, wherein embodiments will be described in detail with reference to the accompanying drawings. The inventive concept, however, may be embodied in various different forms, and should not be construed as being limited only to the illustrated embodiments. Rather, these embodiments are provided as examples so that the inventive concept will be thorough and complete, and will fully convey the concept of the inventive concept to those skilled in the art. The inventive concept may be defined by scope of the claims. Meanwhile, the terminology used herein to describe embodiments of the inventive concept is not intended to limit the scope of the inventive concept.

The terminology used herein is for the purpose of describing embodiments and is not intended to limit the inventive concept. In the specification, the singular forms include plural forms unless particularly mentioned. The terms "comprises" and/or "comprising" used herein does not exclude presence or addition of one or more other elements, in addition to the aforementioned elements. The same reference numerals denote the same elements throughout the specification. As used herein, the term "and/or" includes any and all combinations of one or more of the associated components. It will be understood that, although the terms "first", "second", etc., may be used herein to describe various components, these components should not be limited by these terms. These terms are only used to distinguish one component from another component. Thus, a first component discussed below could be termed a second component without departing from the teachings of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The term "unit" or "module" used herein may refer to software or hardware such as field programmable gate array (FPGA) or application specific integrated circuit (ASIC), and the "unit" or "module" may perform some functions. However, the "unit" or "module" may not be limited to software or hardware. The "unit" or "module" may be configured to exist in an addressable storage medium or may be configured to reproduce one or more processors. Therefore, as an example, "units" or "module" may include various elements such as software elements, object-oriented software elements, class elements, and task elements, processes, functions, attributes, procedures, subroutines, program code segments, drivers, firmware, microcodes, circuits, data, databases, data structures, tables, arrays, and variables. Functions provided in "units" or "modules" and elements may be combined into a smaller number of "units" or "modules" and elements or may be divided into additional "units" or "modules" and elements.

As illustrated in the figures, spatially relative terms, such as "below", "beneath", "lower", "above", "upper", and the like, may be used herein for ease of description to describe the relationship between one component and other components. It will be understood that the spatially relative terms are intended to encompass different orientations of the components in use or operation in addition to the orientation depicted in the figures. For example, when inverting a component shown in the figures, a component described as "below" or "beneath" of another component may be placed "above" another element. Thus, the exemplary term "below" may include both downward and upward directions. The components may also be oriented in different directions, and thus the spatially relative terms may be interpreted depending on orientation.

Hereinafter, embodiments of the inventive concept will be described in detail with reference to accompanying drawings.

FIG. 1 is a block diagram schematically illustrating a temperature providing device, according to an embodiment.

Referring to FIG. 1, a temperature providing device 100 includes a housing body 110, a plurality of temperature transmitters 120, and a temperature adjusting unit 130.

In the meantime, only components associated with embodiments are illustrated in the temperature providing device 100 illustrated in FIG. 1. Accordingly, it may be understood that the temperature providing device 100 further includes general-purpose components in addition to the components illustrated in FIG. 1.

In an embodiment, the temperature providing device 100 further includes a controller (not illustrated) controlling at least part of the plurality of temperature transmitters 120, the temperature adjusting unit 130, and a driving unit 140. The controller may include at least one processor; a single controller may control all of the plurality of temperature transmitters 120, the temperature adjusting unit 130, and the driving unit 140; one or more processors controlling the plurality of temperature transmitters 120, the temperature adjusting unit 130, and the driving unit 140 may be included.

The housing body 110 is configured to house the plurality of temperature transmitters 120 and the temperature adjusting unit 130. The form thereof is not limited.

For example, the housing body 110 houses the plurality of temperature transmitters 120 and the temperature adjusting unit 130; the housing body 110 may be implemented in the form in which an opening is formed on one surface or may be implemented in the form in which one side is opened, to expose at least part of the plurality of temperature transmitters 120 to the outside.

Furthermore, the housing body 110 may be implemented in the form of a box housing the plurality of temperature transmitters 120 and the temperature adjusting unit 130 or may be implemented in the form of a band in which the plurality of temperature transmitters 120 and the temperature adjusting unit 130 are embedded. For example, the band may be made of a material such as rubber or cloth that is easy to mount on the body.

The plurality of temperature transmitters 120 are used to transmit different temperatures to the outside of the housing body 110.

For example, each of the plurality of temperature transmitters 120 may be implemented in the form of a heating plate or pipe that is capable of transmitting specific different temperatures to the outside of the housing body 110.

In an embodiment, each of the plurality of temperature transmitters 120 may transmit temperature through contact; a part of the plurality of temperature transmitters 120 may be located inside the housing body 110; some may be exposed to the outside of the housing body 110 to transmit a specific temperature through contact with an object.

The temperature adjusting unit 130 adjusts the temperature of each of the plurality of temperature transmitters 120. For example, each of the plurality of temperature transmitters 120 may be implemented in the form of a heating plate; the temperature adjusting unit 130 may adjust the temperature of the heating plate using electricity.

For another example, each of the plurality of temperature transmitters 120 may be implemented in the form of a pipe; the temperature adjusting unit 130 may adjust the temperature of the pipe using electricity. In particular, the temperature adjusting unit 130 may adjust the temperature of the pipe by allowing the water of a specific temperature to flow into the pipe.

Figure 2:
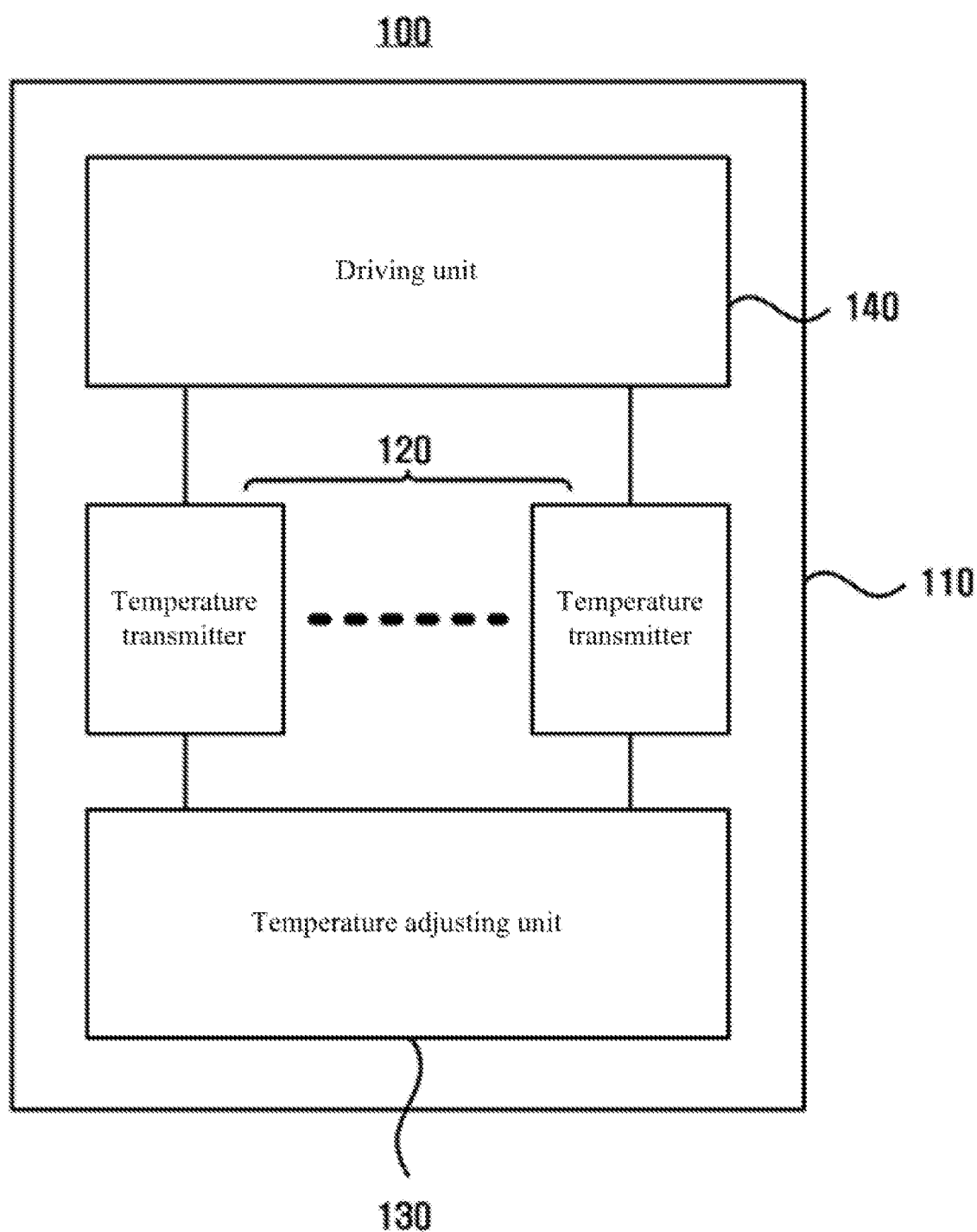
FIG. 2 is a block diagram of a temperature providing device including a driving unit, according to an embodiment.

FIG. 2 is a block diagram of a temperature providing device including a driving unit, according to an embodiment.

Referring to FIG. 2, the temperature providing device 100 includes the housing body 110, the plurality of temperature transmitters 120, the temperature adjusting unit 130, and the driving unit 140.

In the meantime, only components associated with embodiments are illustrated in the temperature providing device 100 illustrated in FIG. 2. Accordingly, it may be understood that the temperature providing device 100 further includes general-purpose components in addition to the components illustrated in FIG. 2.

In an embodiment, the temperature providing device 100 further includes a controller (not illustrated) controlling at least part of the plurality of temperature transmitters 120, the temperature adjusting unit 130, and the driving unit 140. The controller may include at least one processor; a single controller may control all of the plurality of temperature transmitters 120, the temperature adjusting unit 130, and the driving unit 140; one or more processors controlling the plurality of temperature transmitters 120, the temperature adjusting unit 130, and the driving unit 140 may be included.

The temperature providing device 100 illustrated in FIG. 2 refers to an embodiment in which the driving unit 140 is included in the temperature providing device 100 illustrated in FIG. 1. Accordingly, even though omitted with regard to the temperature providing device 100 illustrated in FIG. 2 and the components thereof, the contents described with respect to the temperature providing device 100 illustrated in FIG. 1 and the components thereof is applied to the temperature providing device 100 illustrated in FIG. 2 and the components thereof.

In an embodiment, the driving unit 140 is used to move the plurality of temperature transmitters 120. For example, the driving unit 140 may include, but is not limited to, at least one motor.

In an embodiment, the driving unit 140 includes an MR compact motor and may be configured to use the temperature providing device 100 according to the disclosed embodiment even in the MR device.

The driving unit 140 exposes at least part of the plurality of temperature transmitters 120 to the outside of the housing body 110, using vertical movement, rotational movement, or tilting movement.

In an embodiment, the temperature providing device 100 is mounted on the body. The temperature providing device 100 is mounted on the body by forming an opening such that at least part of the plurality of temperature transmitters 120 is capable of being exposed to the outside or such that the opened surface faces the body.

The driving unit 140 exposes at least part of the plurality of temperature transmitters 120 to the outside of the housing body 110 to contact the body and separates the rest of the plurality of temperature transmitters 120, which is not exposed, from the body.

The driving unit 140 may alternately expose the plurality of temperature transmitters 120 to the exterior of the housing body 110 and may allow the temperature transmitters 120 exposed to the outside of the housing body 110 to contact the body.

In an embodiment, the plurality of temperature transmitters 120 is set to have different temperatures, respectively; the driving unit 140 alternately exposes each of the plurality of temperature transmitters 120 having different temperatures to the outside of the housing body 110; accordingly, the driving unit 140 allows different temperatures to be alternately provided to the outside of the housing body 110.

In an embodiment, the driving unit 140 alternately exposes each of the plurality of temperature transmitters 120 having different temperatures to the outside of the housing body 110 at a high speed; accordingly, the driving unit 140 allows different temperatures to be alternately provided to the outside of the housing body 110 at a high speed.

Figure 3:
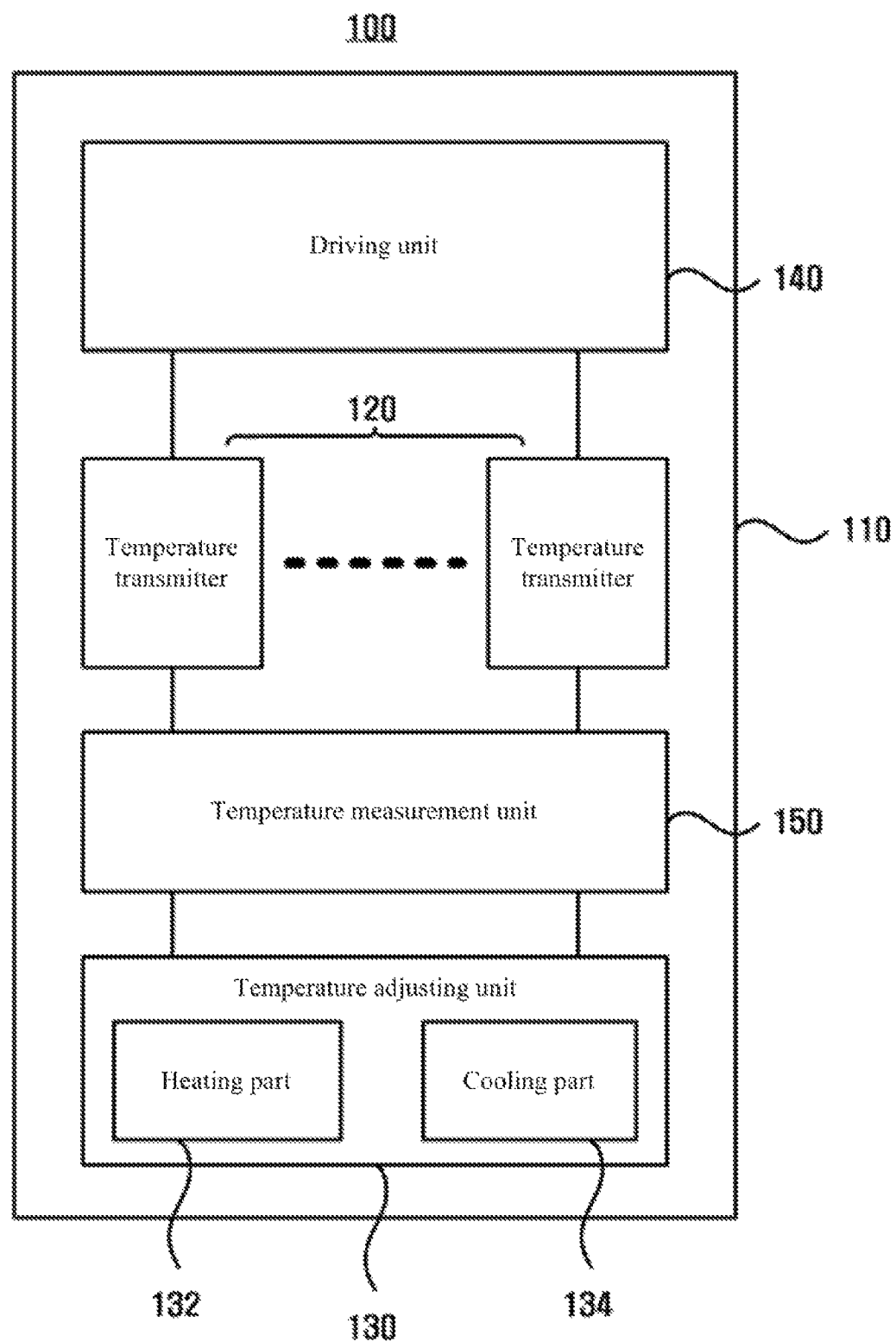
FIG. 3 is a block diagram of a temperature providing device including a temperature measurement unit, according to an embodiment.

FIG. 3 is a block diagram of a temperature providing device including a temperature measurement unit, according to an embodiment.

Referring to FIG. 3, the temperature providing device 100 includes the housing body 110, the plurality of temperature transmitters 120, the temperature adjusting unit 130, the driving unit 140, and a temperature measurement unit 150; the temperature adjusting unit 130 includes a heating part 132 and a cooling part 134.

In the meantime, only components associated with embodiments are illustrated in the temperature providing device 100 illustrated in FIG. 3. Accordingly, it may be understood that the temperature providing device 100 further includes general-purpose components in addition to the components illustrated in FIG. 3.

In an embodiment, the temperature providing device 100 further includes a controller that controls at least part of the plurality of temperature transmitters 120, the temperature adjusting unit 130, the driving unit 140, and the temperature measurement unit 150. The controller may include at least one processor; a single controller may control all of the plurality of temperature transmitters 120, the temperature adjusting unit 130, the driving unit 140, and the temperature measurement unit 150; one or more processors controlling the plurality of temperature transmitters 120, the temperature adjusting unit 130, the driving unit 140, and the temperature measurement unit 150 may be included. For example, the controller may determine a specific temperature to be transmitted to the outside (e.g., the body of a patient with chronic pain) of the housing body 110 and may expose a temperature transmitter having the specific temperature determined among the plurality of temperature transmitters 120 to the outside of the housing body 110 (e.g., the contact with the body of a patient with chronic pain).

The temperature providing device 100 illustrated in FIG. 3 refers to an embodiment in which the temperature measurement unit 150, the heating part 132, and the cooling part 134 are included in the temperature providing device 100 illustrated in FIG. 2. Accordingly, even though omitted with regard to the temperature providing device 100 illustrated in FIG. 3 and the components thereof, the contents described with respect to the temperature providing device 100 illustrated in FIGS. 1 and 2 and the components thereof is applied to the temperature providing device 100 illustrated in FIG. 3 and the components thereof.

In an embodiment, the temperature providing device 100 includes the temperature measurement unit 150 for measuring the temperature of each of the plurality of temperature transmitters 120. The temperature measurement unit 150 includes at least one sensor for measuring the temperature of each of the plurality of temperature transmitters 120. The temperature measurement unit 150 may include a plurality of sensors, which are respectively in contact with or close to the plurality of temperature transmitters 120. The temperature measurement unit 150 may transmit the temperature of each of the plurality of temperature transmitters 120 to a controller; when the actual temperature of the temperature transmitter 120 having the specific temperature determined among the plurality of temperature transmitters 120 is different from the determined specific temperature, the controller may control the temperature adjusting unit 130 such that the actual temperature of the temperature transmitter 120 with the determined specific temperature has the determined specific temperature (feedback control).

In an embodiment, the temperature adjusting unit 130 includes the heating part 132 increasing the temperature of each of the plurality of temperature transmitters 120 and the cooling part 134 decreasing the temperature of each of the plurality of temperature transmitters 120.

In an embodiment, the cooling part 134 includes at least one cooling fan. The cooling part 134 may lower the temperature of the temperature transmitter 120 composed of a heating plate or pipe, using the cooling fan.

In another embodiment, the cooling part 134 may lower the temperature of the temperature transmitter 120, using water. For example, the cooling part 134 may lower the temperature of the temperature transmitter 120 by allowing water to flow into the temperature transmitter composed of the pipe.

The temperature adjusting unit 130 may adjust each of the temperature transmitters 120 to maintain the specific temperature, using the temperature of each of the plurality of temperature transmitters 120 measured by the temperature measurement unit 150.

Accordingly, each of the plurality of temperature transmitters 120 may be maintained to have different specific temperatures. Furthermore, the temperature of each of the plurality of temperature transmitters 120 may be changed to temperatures different from each other.

Figure 4:
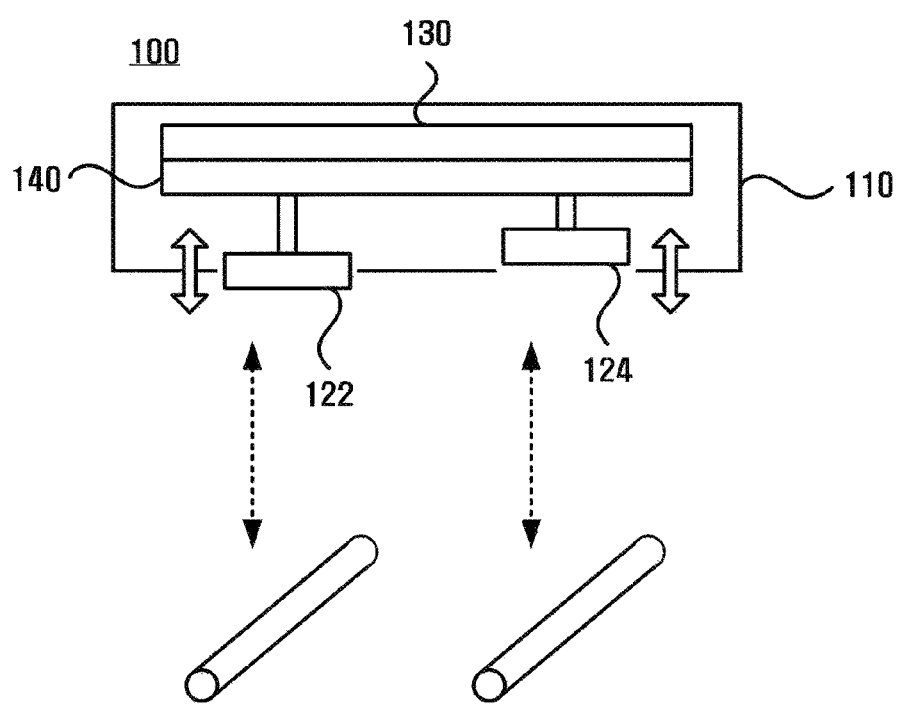
FIG. 4 is a view illustrating an example of a temperature transmitting device including two temperature transmitters.

FIG. 4 is a view illustrating an example of a temperature transmitting device including two temperature transmitters.

Referring to FIG. 4, a temperature transmitting device 100 including the housing body 110, a first temperature transmitter 122, a second temperature transmitter 124, the temperature adjusting unit 130, and the driving unit 140 are illustrated.

The temperature adjusting unit 130 sets the first temperature transmitter 122 to the first temperature and sets the second temperature transmitter 124 to the second temperature different from the first temperature.

The driving unit 140 alternately exposes the first temperature transmitter 122 and the second temperature transmitter 124 to the outside of the housing body 110.

In an embodiment, the temperature providing device 100 is mounted on the body, and the driving unit 140 alternately contacts or spaces the first temperature transmitter 122 and the second temperature transmitter 124 to or from the body.

The first temperature transmitter 122 and the second temperature transmitter 124 may be implemented in the form of a heating plate and the temperature may be controlled by electricity; the first temperature transmitter 122 and the second temperature transmitter 124 may be implemented in the form of a pipe and the temperature may be controlled by water.

In the meantime, the temperature measurement unit 150 may include a first sensor (not illustrated), which is positioned in the first temperature transmitter 122 and measures the temperature of the first temperature transmitter 122, and a second sensor (not illustrated), which is positioned in the second temperature transmitter 124 and measures the temperature of the second temperature transmitter 124.

The temperature providing device 100 according to the disclosed embodiments may be used for pain treatment or sensory examination of a patient.

For example, according to an embodiment, the temperature providing device 100 disclosed in the training for the treatment of patients with chronic pain may be used. Because diabetic patients often feel chronic pain, the training using the temperature providing device 100 according to the disclosed embodiments may be widely used.

For another example, when it is necessary to investigate the function of the sensory nerves of a patient, the temperature providing device 100 according to the disclosed embodiment may be used. Because stroke patients often experience paralysis, the function of the sensory nerve may be tested using the temperature providing device 100 according to the disclosed embodiment.

There is a nerve fiber, which is reflected only when fast and sharp temperature changes occur, in the body. Accordingly, the training may be performed to treat patients with chronic pain, using a device that rapidly changes temperature at a specific interval.

The temperature providing device 100 may be manufactured in the form of a box to contact the patient's body; the temperature providing device 100 may quickly test the patient's sensory nerves by providing different temperatures quickly and alternately.

Furthermore, the temperature providing device 100 may be implemented in the form of a band and may be mounted on the patient's body; the temperature providing device 100 may be used to train the patient by providing different temperatures quickly and alternately.

Referring to FIG. 4, the temperature providing device 100 may vertically and alternately move the first temperature transmitter 122 and the second temperature transmitter 124 and may expose or house each of the first temperature transmitter 122 and the second temperature transmitter 124 to the outside of the housing body 110; accordingly, the temperature providing device 100 may contact or space each of the first temperature transmitter 122 and the second temperature transmitter 124 to or from the body.

As illustrated in FIG. 4, the temperature providing device 100 including two temperature transmitters may be mounted on the patient's body and may be used for the training for the treatment of chronic pain by providing two different temperatures alternately and repeatedly.

In the meantime, the temperature measurement unit 150 may include a first sensor (not illustrated), which is positioned in the first temperature transmitter 122 and measures the temperature of the first temperature transmitter 122, and a second sensor (not illustrated), which is positioned in the second temperature transmitter 124 and measures the temperature of the second temperature transmitter 124.

Figure 5:
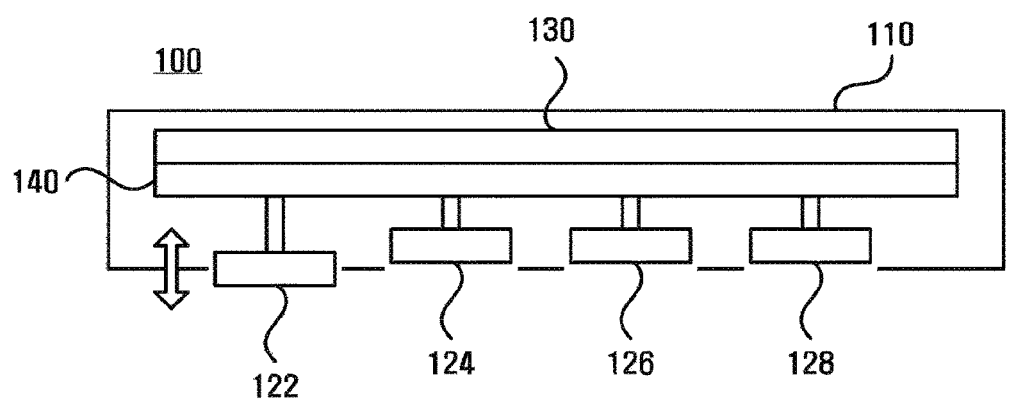
FIG. 5 is a view illustrating an example of a temperature transmitting device including a plurality of temperature transmitters.

FIG. 5 is a view illustrating an example of a temperature transmitting device including a plurality of temperature transmitters.

Referring to FIG. 5, the temperature transmitting device 100 including the housing body 110, the first temperature transmitter 122, the second temperature transmitter 124, a third temperature transmitter 126, a fourth temperature transmitter 128, the temperature adjusting unit 130, and the driving unit 140 is illustrated.

In an embodiment, the temperature adjusting unit 130 may set each of the first to fourth temperature transmitters 122 to 128 to have different temperatures.

Each of the first to fourth temperature transmitters 122 to 128 may be set to sequentially have different temperatures in ascending or descending order or may be set to have different temperatures regardless of the order.

For the purpose of testing the patient's sense, the temperature providing device 100 illustrated in FIG. 5 may be configured to provide several temperatures simultaneously or sequentially one by one, or to provide one or more temperatures alternately at the same time.

The driving unit 140 may move the first to fourth temperature transmitters 122 to 128 vertically; accordingly, the driving unit 140 may expose or house at least part of the first to fourth temperature transmitters 122 to 128 to the outside of the housing body 110 or may contact or space at least part of the first to fourth temperature transmitters 122 to 128 to or from the body.

In the meantime, the temperature measurement unit 150 may include a first sensor (not illustrated), which is positioned at the first temperature transmitter 122 and measures the temperature of the first temperature transmitter 122, a second sensor (not illustrated), which is positioned at the second temperature transmitter 124 and measures the temperature of the second temperature transmitter 124, a third sensor (not illustrated), which is positioned at the third temperature transmitter 126 and measures the temperature of the third temperature transmitter 126, and a fourth sensor (not illustrated), which is positioned at the fourth temperature transmitter 128 and measures the temperature of the fourth temperature transmitter 128.

Figure 6:
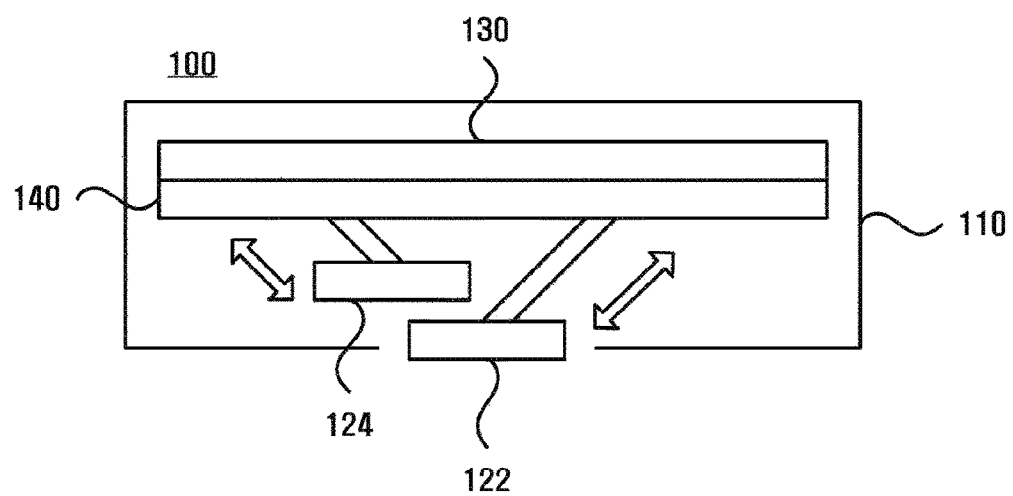
FIG. 6 is a view illustrating an example of a temperature providing device capable of providing different temperatures at the same location.

FIG. 6 is a view illustrating an example of a temperature providing device capable of providing different temperatures at the same location.

Referring to FIG. 6, the temperature transmitting device 100 including the housing body 110, the first temperature transmitter 122, the second temperature transmitter 124, the temperature adjusting unit 130, and the driving unit 140 are illustrated.

The temperature transmitting device 100 illustrated in FIGS. 4 and 5 is configured to provide different temperatures at different locations adjacent to each other.

The temperature transmitting device 100 illustrated in FIG. 6 is configured such that each of the first temperature transmitter 122 and the second temperature transmitter 124 are capable of providing different temperatures at the same position through one opening.

According to an embodiment, the temperature providing device 100 illustrated in FIG. 6 may be used when it is necessary to alternately provide temperatures, which are different from each other, at the same location.

The temperature providing device 100 illustrated in FIG. 6 is configured such that the first temperature transmitter 122 and the second temperature transmitter 124 provide different temperatures at the same position by using a vertical movement method in an oblique direction. However, the method in which the temperature providing device 100 alternately exposes the first temperature transmitter 122 and the second temperature transmitter 124 to the outside of the housing body 110 is not limited thereto.

For example, the temperature providing device 100 may allow the first temperature transmitter 122 and the second temperature transmitter 124 to be alternately exposed to the outside of the housing body 110 by rotating the first temperature transmitter 122 and the second temperature transmitter 124 about one axis.

In the meantime, the temperature measurement unit 150 may include a first sensor (not illustrated), which is positioned in the first temperature transmitter 122 and measures the temperature of the first temperature transmitter 122, and a second sensor (not illustrated), which is positioned in the second temperature transmitter 124 and measures the temperature of the second temperature transmitter 124.

Figure 7:
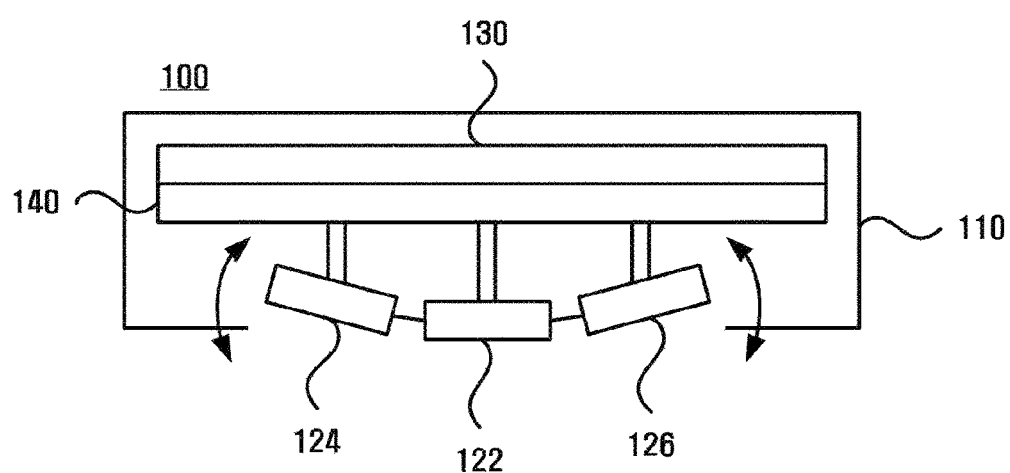
FIG. 7 is a view illustrating an example of a temperature providing device using a rolling movement.

FIG. 7 is a view illustrating an example of a temperature providing device using a rolling movement.

FIGS. 4 to 6 illustrate an embodiment associated with the temperature providing device 100 that exposes a plurality of temperature transmitters to the outside or contacts the plurality of temperature transmitters to the body, using vertical movement.

FIG. 7 illustrates an embodiment associated with the temperature providing device 100 that exposes a plurality of temperature transmitters to the outside or contacts the plurality of temperature transmitters to the body, using rolling movement.

Referring to FIG. 7, the temperature providing device 100 including the housing body 110, the first temperature transmitter 122, the second temperature transmitter 124, the third temperature transmitter 126, the temperature adjusting unit 130, and the driving unit 140 is illustrated.

Each of the first temperature transmitter 122, the second temperature transmitter 124, and the third temperature transmitter 126 is connected to have a predetermined angle with one another.

In the embodiment illustrated in FIG. 7, the configuration using three temperature transmitters 122 to 126 is illustrated. However, the number of temperature transmitters capable of being used in the temperature transmitting device 100 is not limited thereto.

The temperature adjusting unit 130 adjusts the first temperature transmitter 122 to the third temperature transmitter 126 to have temperatures different from one another.

The driving unit 140 may control the first to third temperature transmitters 122 to 126, which are connected to one another to have at a predetermined angle, to be alternately exposed to the outside of the housing body 110 using a rolling movement.

According to an embodiment, the temperature providing device 100 illustrated in FIG. 7 may be implemented in the form of a band to be worn on the body and the different temperatures may be stably provided through the rolling movement; accordingly, the temperature providing device 100 may be used for the training for the treatment of chronic pain.

In the meantime, the temperature measurement unit 150 may include a first sensor (not illustrated), which is positioned at the first temperature transmitter 122 and measures the temperature of the first temperature transmitter 122, a second sensor (not illustrated), which is positioned at the second temperature transmitter 124 and measures the temperature of the second temperature transmitter 124, and a third sensor (not illustrated), which is positioned at the third temperature transmitter 126 and measures the temperature of the third temperature transmitter 126.

Figure 8:
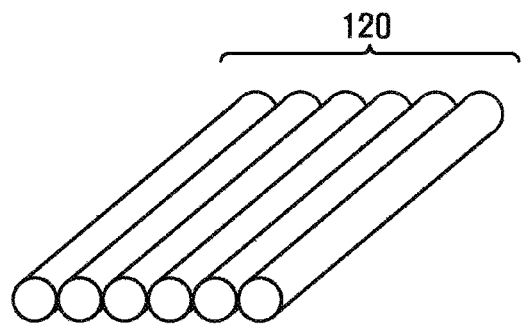
FIG. 8 is a view illustrating a temperature transmitter 120 using a pipe, according to an embodiment.

FIG. 8 is a view illustrating the temperature transmitter 120 using a pipe, according to an embodiment.

In an embodiment, each of the plurality of temperature transmitters 120 may be composed of a pipe made of a material having high thermal conductivity.

The temperature adjusting unit 130 illustrated in FIGS. 1 to 7 may allow the water of different temperatures to flow into each of the plurality of temperature transmitters 120 and thus may allow each of the plurality of temperature transmitters 120 to provide different temperatures to the outside.

The temperature providing device 100 illustrated in FIGS. 2 to 7 may have a configuration that alternately exposes each of the plurality of temperature transmitters 120 to the outside of the temperature providing device 100 using the driving unit 140 and to contact or space each of the plurality of temperature transmitters 120 to or from the body.

On the other hand, according to an embodiment, in the temperature transmitter 120 illustrated in FIG. 8, a plurality of pipes may be exposed together on the outside of the housing body 110 and may be in contact with the body at the same time.

The temperature adjusting unit 130 may allow the water of different temperatures to flow into each pipe and thus may allow the different temperatures to be provided to the outside or the body.

Each pipe included in the temperature transmitter 120 may be implemented such that the temperature similar to the temperature of water flowing through the pipe is transmitted to the outside or the body with a small loss rate because of the high thermal conductivity of each pipe and residual heat is not nearly left after the transmission.

Accordingly, the temperature providing device 100 may alternately provide different temperatures to the outside, using a plurality of pipes included in the temperature transmitter 120 and the water having different temperatures flowing through each pipe.

In the meantime, the temperature measurement unit 150 may include at least one sensor, which is positioned at each of the plurality of temperature transmitters 120 and measures the temperature of each of the plurality of temperature transmitters 120.

Moreover, the temperature providing device 100 according to the disclosed embodiments may be used for the pain improvement training of patients with chronic pain.

In this specification, the pain improvement training' refers to the training for the specific number of trials to select a temperature (e.g., high temperature or low temperature) that satisfies a specific condition among first and second temperatures different from each other.

In this specification, 'expected threshold temperature' refers to the temperature estimated as the threshold temperature by the computer to set the first temperature or the second temperature.

In this specification, 'evaluation threshold temperature' refers to the temperature determined as a user's actual pain threshold.

In this specification, 'reference temperature interval' refers to the value applied as the difference value between the first temperature and the second temperature, as the temperature difference at which the user is capable of detecting the temperature difference.

In an embodiment, the temperature providing device 100 provides the first temperature to the first body point of a patient and provides the second temperature to the second body point, depending on the commands of a controller or an external computer. The computer requests the patient to select the temperature matched with a specific condition among the first temperature and the second temperature and calculates a correct answer rate by performing pain improvement training using the selection result; the pain improvement training is to perform the specific number of trials for distinguishing the first temperature and the second temperature.

In an embodiment, the first temperature and the second temperature are provided to the first body point and the second body point, simultaneously or sequentially. The first body point and the second body point may be the same body point. In this case, the first temperature and the second temperature are sequentially provided to the same body point.

Moreover, various methods are applied to a method of setting the first temperature and the second temperature. In an embodiment, the computer determines the expected threshold temperature expected as the threshold, and sets the first and second temperatures based on the expected threshold temperature. As a specific example, the computer sets the first temperature to a temperature the same as the expected threshold temperature or lower than the expected threshold temperature by a specific value and sets the second temperature to a temperature higher than the first temperature by a reference temperature interval. At this time, the specific value for setting the first temperature refers to a value for setting a temperature lower than the expected threshold temperature to the first temperature while the value approximates the expected threshold temperature, as a value less than the reference temperature interval.

Also, in another specific example, the computer sets the reference temperature (i.e., the expected threshold temperature) to the first temperature, sets the second temperature to a plurality of temperatures higher or lower than the first temperature, and requests the patient to determine which stimulus is higher among the stimulus of the first temperature and the stimulus of the second temperature presented to the patient. The order in which the first and second temperatures are presented may be a random order (i.e., the order in which the first and second temperatures are presented in each training trial may not be determined). Furthermore, training difficulty may be increased by reducing the difference between the first temperature and the second temperature.

Afterward, the computer requests a user to select temperature matched with a specific condition, among the first temperature and the second temperature. For example, the computer may request the user to select high or low temperature among the first temperature and the second temperature. In an embodiment, when the computer provides the first temperature and the second temperature sequentially, the computer provides (e.g., guide a point in time when the first temperature and the second temperature are provided through the method of providing visual information on a screen or providing auditory information) identification information to the user at a point in time when the first temperature and the second temperature are provided, and receives the selection of options corresponding to a specific condition (e.g., high temperature or low temperature) from the user.

In another embodiment, when different temperature points (i.e., the first temperature and the second temperature) are provided to different body points by the temperature providing device 100, the computer receives the selection of options corresponding to a specific condition (e.g., high temperature or low temperature) from the user based on the location.

The computer calculates the correct answer rate by performing the pain improvement training depending on the selection result. The pain improvement training is to perform the specific number of trials for distinguishing the first temperature and the second temperature. The computer calculates the correct answer rate based on the correct answer entered in a plurality of trials. The computer determines whether the user correctly distinguishes the first temperature and the second temperature, through the correct answer rate.

In another embodiment, when the correct answer rate is not greater than a reference condition, the computer repeatedly provides the training of distinguishing between the first temperature and the second temperature of the same condition.

In another embodiment, the computer adjusts (sets again) the first temperature and the second temperature based on the correct answer rate. For example, the computer increases the first temperature and the second temperature to increase the user's pain threshold. When the first temperature and the second temperature are set to the expected threshold temperature as the reference, the computer adjusts the expected threshold temperature based on the correct answer rate. When the correct answer rate is high, the computer may increase the interval of temperature adjustment (e.g. increase the expected threshold temperature).

Moreover, the computer adjusts a reference temperature interval based on the expected threshold temperature. The difficulty of training provided to the patient may be adjusted by adjusting the reference temperature interval corresponding to the difference between the first temperature and the second temperature. For example, the training of distinguishing between relatively great temperature differences may be provided patients with severe chronic pain by increasing the reference temperature interval; the training with the high difficulty of temperature discrimination may be provided to patients with mild chronic pain by decreasing the reference temperature interval.

In another embodiment, in the case of setting the first temperature and the second temperature based on the expected threshold temperature, it is possible to adjust the expected threshold temperature by a reference interval after the specific number of training is performed, and to determine an evaluation threshold temperature based on the correct answer rate at each expected threshold temperature. The computer calculates the evaluation threshold temperature corresponding to the user's actual pain threshold, based on the result of performing the training on several expected threshold temperatures.

In the above, for example, providing a user with the first temperature and the second temperature is described as the pain improvement training method according to an embodiment of the inventive concept. However, the technical spirit of the pain improvement training method according to an embodiment of the inventive concept is not limited thereto; as long as the user is provided with a plurality of temperatures different from each other, it should be interpreted as being included in the technical spirit of the pain improvement training method according to an embodiment of the inventive concept. For example, the pain improvement training method according to an embodiment of the inventive concept may provide the user with the first temperature, the second temperature, and the third temperature, which are different from one another, or may provide the user with the first temperature, the second temperature, the third temperature, and the fourth temperature, which are different from one another. In this case, the specific training method for providing the user with a plurality of different temperatures may be applied by inferring the details of the training method for providing the user with the first temperature and the second temperature.

The steps of a method or algorithm described in connection with the embodiments of the inventive concept may be embodied directly in hardware, in a software module executed by hardware, or in a combination thereof. The software module may reside on a Random Access Memory (RAM), a Read Only Memory (ROM), an Erasable Programmable ROM (EPROM), an Electrically Erasable Programmable ROM (EEPROM), a Flash memory, a hard disk, a removable disk, a CD-ROM, or a computer readable recording medium in any form known in the art to which the inventive concept pertains.

The method according to an embodiment of the inventive concept may be implemented by a program (or an application) and may be stored in a medium such that the program is executed in combination with a computer being hardware.

The above-described program may include a code encoded by using a computer language such as C, C++, JAVA, a machine language, or the like, which a processor (CPU) of the computer can read through the device interface of the computer, such that the computer reads the program and performs the methods implemented with the program. The code may include a functional codes associated with the function that defines functions necessary to perform the methods, and may include a control code associated with an execution procedure necessary for the processor of the computer to perform the functions in a predetermined procedure. Furthermore, the code may further include additional information necessary for the processor of the computer to perform the functions or a memory reference-related code associated with the location (address) of the internal or external memory of the computer, at which the media needs to be checked. Moreover, when the processor of the computer needs to communicate with any other remote computer or any other remote server to perform the functions, the code may further include a communication-related code associated with how to communicate with any other remote computer or server using the communication module of the computer, what information or media should be transmitted or received during communication, or the like.

The stored media may mean the media that does not store data for a short period of time such as a register, a cache, a memory, or the like but semi-permanently stores to be read by the device. Specifically, for example, the stored media include, but are not limited to, ROM, RAM, CD-ROM, magnetic tape, floppy disk, optical data storage device, and the like. That is, the program may be stored in various recording media on various servers that the computer can access, or various recording media on the computer of the user. In addition, the media may be distributed to a computer system connected to a network, and a computer-readable code may be stored in a distribution manner.

Although embodiments of the inventive concept have been described herein with reference to accompanying drawings, it should be understood by those skilled in the art that the inventive concept may be embodied in other specific forms without departing from the spirit or essential features thereof. Therefore, the above-described embodiments are exemplary in all aspects, and should be construed not to be restrictive.

According to the disclosed embodiment, it is possible to alternately provide different specific temperatures to the outside.

In particular, according to the disclosed embodiment, delays may be reduced using a plurality of temperature transmitters, and it is possible to alternately provide a constant temperature at a high speed.

According to an embodiment, because different temperatures are alternately provided to the patient's skin surface at a high speed, the temperature providing device according to the disclosed embodiments may be used for training for the treatment of a patient with chronic pain and may also be used for sensory examination of a patient.

The effects of the present inventive concept are not limited to the aforementioned effects, and other effects not mentioned herein will be clearly understood from the following description by those skilled in the art to which the inventive concept pertains.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A temperature providing device, the device comprising:
   a housing body;
   a plurality of temperature transmitters configured to transmit different temperatures to an outside of the housing body;
   a temperature adjusting unit configured to adjust a temperature of each of the plurality of temperature transmitters;
   a controller, wherein the controller is configured to:
   determine a specific temperature to be transmitted to the outside of the housing body; and
   expose a temperature transmitter having the determined specific temperature among the plurality of temperature transmitters to the outside of the housing body; and
   a driving unit configured to move each of the plurality of temperature transmitters,
   wherein the controller is configured to expose the temperature transmitter having the determined specific temperature among the plurality of temperature transmitters to the outside of the housing body, using the driving unit, and
   wherein the temperature providing device is configured to be mounted on a body, and the controller is configured to expose at least part of the plurality of temperature transmitters to the outside of the housing body by using the driving unit to contact the at least part of the plurality of temperature transmitters to the body and to space a rest of the plurality of temperature transmitters, which are not exposed, from the body.

2. The device of claim 1, wherein the temperature transmitter includes at least one heating plate, and
   wherein the temperature adjusting unit is configured to adjust a temperature of the heating plate, using electricity.

3. The device of claim 2, wherein the driving unit includes at least one motor, and
   wherein the controller is configured to expose a heating plate having the specific temperature to the outside of the housing body by rotating the at least one heating plate using the motor.

4. The device of claim 1, wherein the temperature transmitter includes at least one pipe, and
   wherein the temperature adjusting unit is configured to adjust a temperature of the pipe, using water.

5. The device of claim 1, wherein the temperature adjusting unit includes:
   a heating part for increasing a temperature of the temperature transmitter; and
   a cooling part for decreasing the temperature of the temperature transmitter.

6. The device of claim 5, wherein the cooling part includes at least one cooling fan.

7. The device of claim 1, further comprising:
   a temperature measurement unit configured to measure the temperature of each of the plurality of temperature transmitters.

8. A temperature providing device, the device comprising:
   a housing body;
   a plurality of temperature transmitters configured to transmit different temperatures to an outside of the housing body;
   a temperature adjusting unit configured to adjust a temperature of each of the plurality of temperature transmitters;
   a controller, wherein the controller is configured to:
   determine a specific temperature to be transmitted to the outside of the housing body; and
   expose a temperature transmitter having the determined specific temperature among the plurality of temperature transmitters to the outside of the housing body; and
   a driving unit configured to move each of the plurality of temperature transmitters,
   wherein the controller is configured to expose the temperature transmitter having the determined specific temperature among the plurality of temperature transmitters to the outside of the housing body, using the driving unit,
   wherein the plurality of temperature transmitters includes a first temperature transmitter and a second temperature transmitter,
   wherein the temperature adjusting unit is configured to set the first temperature transmitter to a first temperature and set the second temperature transmitter to a second temperature different from the first temperature, and
   wherein the controller alternately is configured to expose the first temperature transmitter and the second temperature transmitter to the outside of the housing body, using the driving unit.

9. The device of claim 8, wherein the temperature providing device is mounted on a body, and
   wherein the controller alternately is configured to contact or space the first temperature transmitter and the second temperature transmitter to or from the body, using the driving unit.

10. The device of claim 8, wherein the temperature transmitter includes at least one heating plate, and
    wherein the temperature adjusting unit is configured to adjust a temperature of the heating plate, using electricity.

11. The device of claim 10, wherein the driving unit includes at least one motor, and
    wherein the controller is configured to expose a heating plate having the specific temperature to the outside of the housing body by rotating the at least one heating plate using the motor.

12. The device of claim 8, wherein the temperature transmitter includes at least one pipe, and
    wherein the temperature adjusting unit is configured to adjust a temperature of the pipe, using water.

13. The device of claim 8, wherein the temperature adjusting unit includes:

a heating part for increasing a temperature of the temperature transmitter; and a cooling part for decreasing the temperature of the temperature transmitter.

14. The device of claim 13, wherein the cooling part includes at least one cooling fan.

15. The device of claim 8, further comprising:

a temperature measurement unit configured to measure the temperature of each of the plurality of temperature transmitters.

* * * * *